(12) United States Patent
Sablone

(10) Patent No.: US 11,529,749 B2
(45) Date of Patent: Dec. 20, 2022

(54) PERFORATING APPARATUS OF A WEB, PERFORATING PROCESS AND PRODUCTION MACHINE

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 349 days.

(21) Appl. No.: 16/714,854

(22) Filed: Dec. 16, 2019

(65) Prior Publication Data

US 2020/0206966 A1 Jul. 2, 2020

(30) Foreign Application Priority Data

Dec. 27, 2018 (IT) ........................ 102018000020530

(51) Int. Cl.
*B26F 1/24* (2006.01)
*A61F 13/15* (2006.01)
*B26F 3/08* (2006.01)

(52) U.S. Cl.
CPC .......... *B26F 1/24* (2013.01); *A61F 13/15707* (2013.01); *B26F 3/08* (2013.01)

(58) Field of Classification Search
CPC ......... B26F 1/24; B26F 3/08; A61F 13/15707
See application file for complete search history.

(56) References Cited

U.S. PATENT DOCUMENTS

| | | | | |
|---|---|---|---|---|
| 4,319,589 A | * | 3/1982 | Labbe | A24C 5/607 83/866 |
| 5,554,250 A | * | 9/1996 | Dais | B26D 9/00 156/361 |
| 5,704,101 A | * | 1/1998 | Majors | A61F 13/512 26/18.5 |
| 6,837,956 B2 | * | 1/2005 | Cowell | B26F 1/24 156/519 |
| 8,166,857 B2 | * | 5/2012 | Powell | B26D 5/08 83/886 |
| 11,123,530 B2 | * | 9/2021 | Niitsu | B81C 1/00111 |
| 2003/0121380 A1 | * | 7/2003 | Cowell | A61F 13/15707 83/660 |
| 2004/0044322 A1 | | 3/2004 | Melius | |
| 2004/0164454 A1 | * | 8/2004 | Gartstein | B81C 1/00111 264/293 |
| 2012/0174720 A1 | * | 7/2012 | Powell | G03G 15/6582 83/30 |
| 2012/0276239 A1 | | 11/2012 | Coe et al. | |

FOREIGN PATENT DOCUMENTS

WO  2006103487 A1  10/2006
WO  2017212519 A1  12/2017

OTHER PUBLICATIONS

Search Report dated Jul. 3, 2019. 7 pages.

* cited by examiner

*Primary Examiner* — Omar Flores Sanchez
(74) *Attorney, Agent, or Firm* — RMCK Law Group PLC

(57) ABSTRACT

A perforating apparatus for perforating a web capable of making at least one plurality of holes in a zone of the web in a precise way and without imperfections or lacerations in the web. The present invention also relates to a process for perforating the web capable of making at least one plurality of holes in a zone of the web in an efficient way and without snags occurring. The present invention also relates to a machine for producing sanitary absorbent articles comprising at least one perforating apparatus.

15 Claims, 5 Drawing Sheets

PERFORATING APPARATUS OF A WEB, PERFORATING PROCESS AND PRODUCTION MACHINE

CROSS-REFERENCE TO RELATED APPLICATION

This application claims priority to Italian Patent Application No. 102018000020530 filed Dec. 27, 2018. The disclosure of the above application is incorporated herein by reference in its entirety.

TECHNICAL FIELD

Embodiments of the present invention relate to a perforating apparatus of a web usable in a machine for producing sanitary absorbent articles, such as diapers, diaper-pants, incontinence pads, sanitary pads, or other articles intended to absorb bodily fluids.

In particular, embodiments of the present invention relate to a perforating apparatus of a web capable of making a plurality of holes in a web intended for making sanitary absorbent articles.

The present invention also relates to a process for perforating a web capable of making in a precise and controlled way a plurality of holes in a web, as well as a machine for producing sanitary absorbent articles comprising one or more perforating apparatuses.

BACKGROUND ART

In the production of sanitary absorbent articles, it is known to use webs having one or more zones in which holes have been made which give the sanitary absorbent article particular properties. For example, perforated webs can give breathability, diversified elasticity, or other properties in relation to the desired requirements.

To obtain sanitary absorbent articles, it is known that the webs are purchased already perforated.

That known solution involves high costs, requires lengthy times for loading in machine and for supplying, and necessitates large warehouse spaces and numbers of personnel.

The use of already perforated webs has the further disadvantage that to obtain different portions of an article having different properties it is necessary to use a plurality of webs having different configurations of holes.

That involves limits in terms of production flexibility and notably limits the types of articles which can be made. For example, that is reflected in the impossibility of making articles or batches of articles with different types of holes.

Due to the intrinsic deterioration of the webs over time, the properties of the latter may change up to the point that they are no longer suitable for the production of sanitary absorbent articles. That involves considerable economic losses, aggravated by the burden of having to dispose of the webs which are no longer usable.

Other known solutions provide for the use of perforating apparatuses installed in line which, as well as being bulky, require the web to be stopped, or notably slowed.

That involves a notable overall slowing in the production of the sanitary absorbent articles no longer acceptable due to the technical and commercial requirements of the sector.

Some known solutions use rotating rollers provided with suitable joined together protrusions and between which the web is made to advance. For example, known solutions of this type are described in document US-A-2012/276239 (US'239).

As the web advances, the joined together protrusions of the two rollers engage the web and jointly make a plurality of holes in the web.

Despite the profuse efforts by experts in the sector, such known solutions do not allow the obtainment of holes that are precise and without imperfections.

Due to the rotation of the rollers, the engagement and disengagement of the web by means of the joined together protrusions occur along a curved path substantially tangent to the advancement direction of the web which typically involves a localized variation in the advancing velocity of the web which produces stretching.

In particular, in the case in which the peripheral velocities of the rollers are equal to the advancing velocity of the web, due to the engagement and disengagement of the joined together protrusions with the web along a curved path substantially tangent to the advancement direction, it is known that many of the resulting holes have an elliptical shape.

Document US'239 also mentions the possibility of using plates with perforating elements without specifying the methods of use, or how they are configured to move in relation to the web.

Such known solutions do not allow the precise and controlled making of holes in specific zones of the web, which often prove to be non-uniform, incomplete and with multiple imperfections.

For example, the holes in the web may have unwanted elliptical shapes and/or lacerated and/or stretched portions, or in the worst cases the web may even remain accidentally caught in the perforating apparatus.

Therefore, the need exists to improve and make available a perforating apparatus, a perforating process, as well as a machine for producing sanitary absorbent articles comprising that perforating apparatus of a web which overcome at least one of the disadvantages of the prior art.

One aim of the present invention is to supply a perforating apparatus capable of making holes in a web in line which are precise and without imperfections so as to obtain sanitary absorbent articles corresponding to design expectations with high production rates.

It is an aim of the present invention to supply a perforating apparatus capable of making holes without obstructing the advancement of the web, that is to say, without locally varying the velocity of the web and consequently preventing the holes from having an elliptical shape.

It is also an aim of the present invention to supply a perforating process which allows the obtainment of holes in a web rapidly and as the web advances along an advancement path.

It is a further aim of the present invention to supply a perforating apparatus with compact dimensions and which allows holes to be made in a web as it advances and which simultaneously guarantees the reduced likelihood of it being able to accidentally become caught in the apparatus itself.

A further aim of the present invention is to supply a machine for producing sanitary absorbent articles comprising at least one perforating apparatus which allows deformations to be made in one or more desired zones of the web in a precise and controlled way.

To overcome the disadvantages of the prior art and to obtain these and further aims and advantages, the Applicant has devised, tested and made the present invention.

DISCLOSURE OF THE INVENTION

The present invention is expressed and characterized in the independent claims, while the dependent claims explain other characteristics of the present invention or variants of the main solution idea.

In accordance with the above-mentioned aims, the present invention relates to a perforating apparatus of at least one web advancing along an advancement path at an advancing velocity.

The perforating apparatus comprises at least one first deformation member provided with a plurality of openings and at least one second deformation member provided with a plurality of protruding elements.

In accordance with one aspect of the present invention, the first deformation member and the second deformation member are configured to position themselves at least in a tracking position, wherein the first deformation member and the second deformation member are placed on opposite sides of the advancement path and facing each other.

In accordance with one aspect of the present invention, the first deformation member and the second deformation member are configured to position themselves in a coupling position, wherein the protruding elements are coupled with the openings orthogonally to the advancement path to make, in use, a plurality of holes in a zone of the web.

In the coupling position, in use, the web is clamped between the first deformation member and the second deformation member so that the protruding elements perforate the web.

According to the present invention, the first deformation member and the second deformation member, in the tracking position and in the coupling position, are configured to advance along a portion parallel to the advancement path at the advancing velocity so as to make the plurality of holes with relative velocities, at least along the advancement path, between the first deformation member and the web and between the second deformation member and the web which are substantially zero.

The present invention allows the making of holes in a web in a precise and controlled way, without the resulting holes having unwanted shapes, simultaneously guaranteeing that the web is not lacerated and proceeds at the advancing velocity of the web without slowing or jamming.

The present invention overcomes the problems relative to the known solutions which use pairs of rollers which do not allow the obtainment of precise and circular holes. Although there are known solutions which use plates with perforating elements, they are not capable of making holes with a circular shape and without instantaneously slowing the advancing of the web at least in correspondence with the engagement zone of the perforating elements with the web.

The known solutions which use plates with perforating elements engage the moving web with those elements starting from a standstill and therefore at the moment of engagement the web is locally slowed causing elongation of the holes in the web.

Thanks to the present invention, it is possible to rapidly obtain perforated zones on the webs in line and having the desired shape, without using already perforated webs.

Thanks to the present solution, not using already perforated webs, it is possible to make the desired pluralities of holes in the desired zones, avoiding having to shape already perforated webs which typically may involve considerable quantities of waste.

In accordance with possible embodiments, the first deformation member comprises a first plate wherein the openings are present.

According to possible embodiments, the second deformation member comprises a second plate wherein the protruding elements are present.

According to possible embodiments, the perforating apparatus comprises disengaging means interposed between the first deformation member and the second deformation member in the coupling position configured to disengage the web from the protruding elements so that, in use, the perforated web is freed from the protruding elements.

In accordance with possible embodiments, the disengaging means comprise at least one disengaging element provided with at least one through opening wherein in the coupling position the protruding elements are inserted.

According to possible embodiments, the disengaging element may comprise a plurality of through openings.

According to possible embodiments, the perforating apparatus comprises a heating device configured to heat the protruding elements.

In accordance with possible embodiments, the perforating apparatus comprises retaining means placed along two directions parallel to the advancement path, arranged laterally to the zone of the web wherein, in use, the holes are made.

According to possible embodiments, in use, the retaining means are configured to position themselves in contact with the web for retaining the web in contact with the first deformation member or the second deformation member.

According to possible embodiments, the perforating apparatus may comprise a plurality of first deformation members and a plurality of said second deformation members, wherein each of the first deformation members and of the second deformation members is configured to move independently of the others.

According to possible embodiments, part of the surface of the first deformation member oriented, in the tracking position, towards the second deformation member is coated with a coating.

In accordance with possible embodiments, the coating may comprise silicone material.

According to possible embodiments, the first deformation member and/or the second deformation member are configured to position themselves along a direction transverse to the advancement path so that the first deformation member and the second deformation member are at least partially overlapping each other. For example, the first deformation member and the second deformation member may be entirely overlapping each other and staggered along the direction transverse to the advancement path of the web, while the web advances along the advancement path.

According to possible embodiments, the first deformation member and/or the second deformation member are configured to position themselves along a direction transverse to the advancement path so that the first deformation member and the second deformation member are partially overlapping each other. For example, the first deformation member and the second deformation member may be partially overlapping each other, while the web advances along the advancement path.

According to possible embodiments, the present invention also relates to a process for perforating at least one web, comprising:
  advancing the web along an advancement path at an advancing velocity;
  positioning at least one first deformation member provided with a plurality of openings and at least one second deformation member provided with a plurality of protruding elements in a tracking position, wherein the first deformation member and the second deformation member are placed on opposite sides of the advancement path and facing each other facing towards two opposite surfaces of said web;

advancing the first deformation member and the second deformation member along a portion parallel to the advancement path at the advancing velocity, so that the relative velocities, at least along the advancement path, between the first deformation member and the web and between the second deformation member and the web are substantially zero;

positioning the first deformation member and the second deformation member in a coupling position, wherein the protruding elements are coupled with the openings orthogonally to the advancement path with the web interposed between them to make a plurality of holes in a zone of the web, while the first deformation member and the second deformation member advance at the advancing velocity along a portion parallel to the advancement path so that the relative velocities remain substantially zero.

In accordance with possible embodiments, the perforating process provides that the first deformation member and/or the second deformation member are positioned along a direction transverse to the advancement path so that the first deformation member and the second deformation member are at least partially overlapping each other to couple with the web and make the plurality of holes in a zone of the web, wherein the zone extends along the transverse direction for an extension less than the transverse extension of the web relative to the advancement path.

In accordance with possible embodiments, the perforating process provides that the first deformation member and/or the second deformation member are positioned along a direction transverse to the advancement path so that the first deformation member and the second deformation member are partially overlapping each other to couple with the web and make the plurality of holes in a zone of the web, wherein the zone extends along the transverse direction for an extension less than the transverse extension of the web relative to the advancement path.

According to possible embodiments, the perforating process provides that protruding elements are heated by means of a heating device.

According to possible embodiments, the perforating process provides that disengaging means separate the web from the protruding elements so as to free the web from the protruding elements.

According to possible embodiments, the perforating process provides that retaining means position themselves in contact with the web along two directions parallel to the advancement path, arranged laterally to the zone of the web wherein holes are made to retain the web in contact with the first deformation member or the second deformation member.

According to possible embodiments, the present invention also relates to a machine for producing sanitary absorbent articles comprising at least one perforating apparatus according to any of the possible embodiments.

DESCRIPTION OF THE DRAWINGS

These and other characteristics of the present invention will be apparent from the following description of embodiments, supplied by way of example only, non-limiting, with reference to the appended drawings wherein.

For easier understanding, identical reference numbers have been used, where possible, to identify identical elements common to the figures. It shall be understood that elements and characteristics of one embodiment may be appropriately incorporated in other embodiments without further explanations.

DESCRIPTION OF EMBODIMENTS

Embodiments described herein, with reference to the figures, relate to a perforating apparatus 10 of at least one web 11 advancing along an advancement path P at an advancing velocity to make a plurality of holes 13 in one or more zones of the web 11 itself.

According to possible embodiments the advancement path P may comprise a straight portion. According to possible embodiments the advancement path P may comprise a curved portion. According to possible embodiments the advancement path P may comprise a portion inclined with respect to a horizontal geometric plane.

As will be clear in the course of the description, the present invention allows holes 13 to be made in a web 11 in a precise and controlled way, that is to say, making them according to the design expectations and without imperfections.

Figure 1:
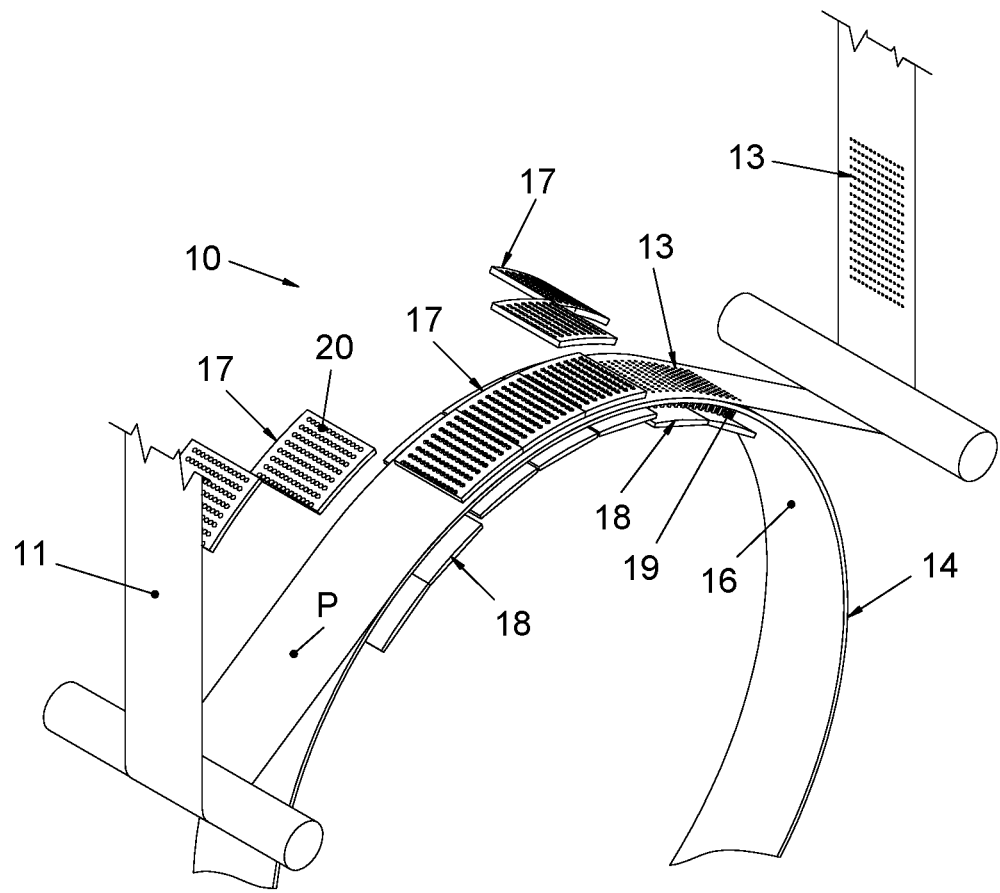
FIG. 1 schematically illustrates a perforating apparatus according to a possible embodiment of the present invention.
Figure 2:
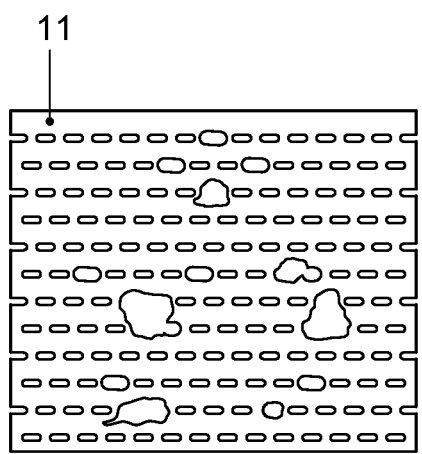
FIG. 2 schematically illustrates a portion of web wherein a plurality of holes is present which are made with a prior art perforating apparatus.

For example, with reference to FIG. 2, the web 11 has a plurality of holes made according to the prior art and which has many imperfections, such as lacerations, stretching of the web 11, holes which are non-uniform and/or with elongate profiles, or other.

Figure 3:
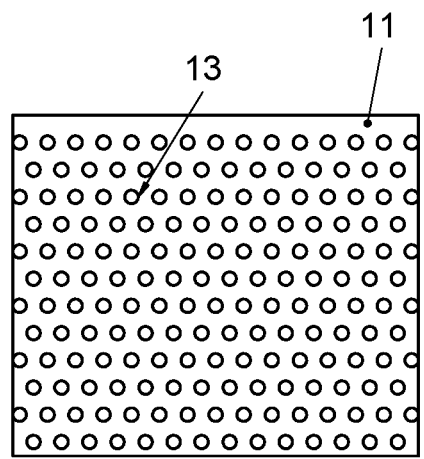
FIG. 3 schematically illustrates a portion of web wherein a plurality of holes is present which are made with a perforating apparatus according to a possible embodiment of the present invention.
Figure 4:
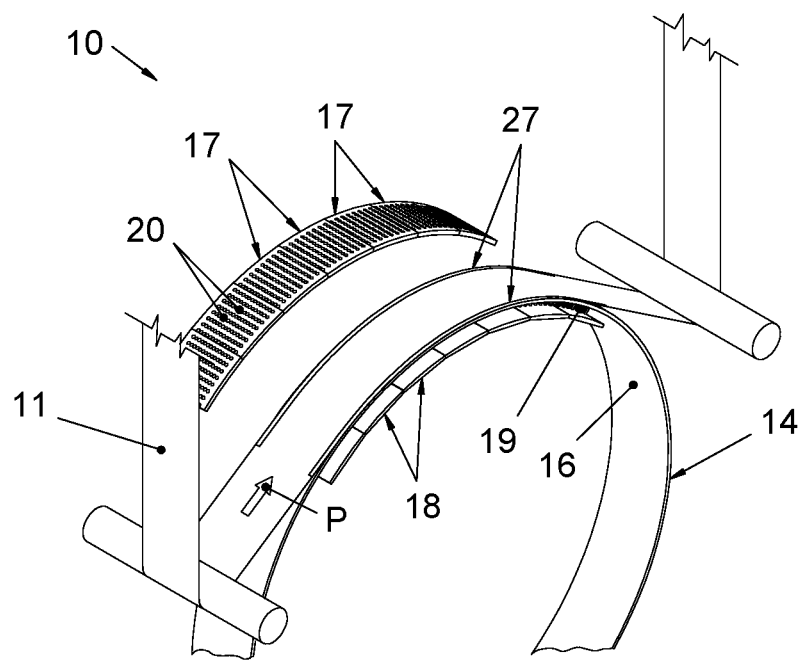
FIGS. 4-7 schematically illustrate a perforating apparatus in various operating steps according to a possible embodiment of the present invention.
Figure 5:
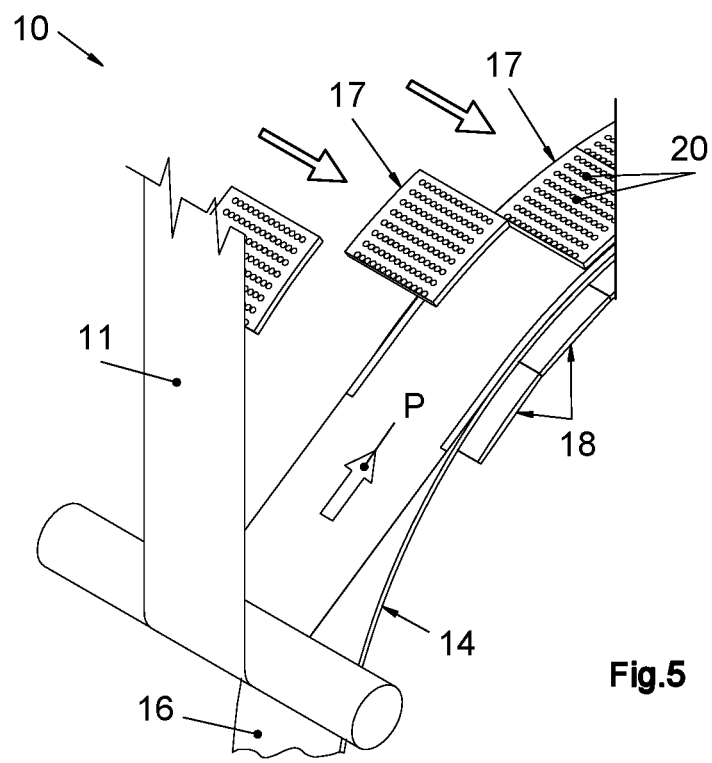
Figure 6:
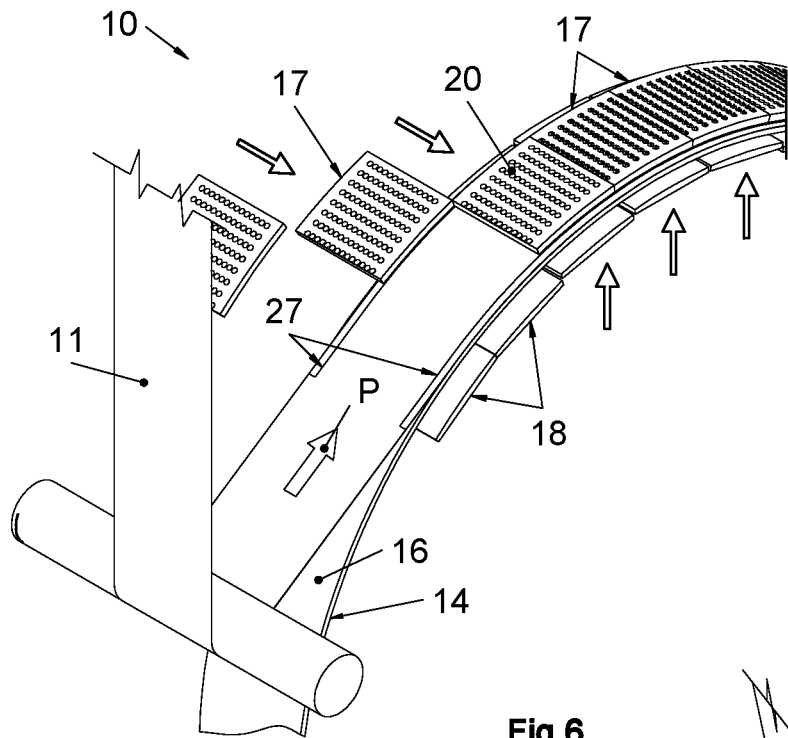
Figure 7:
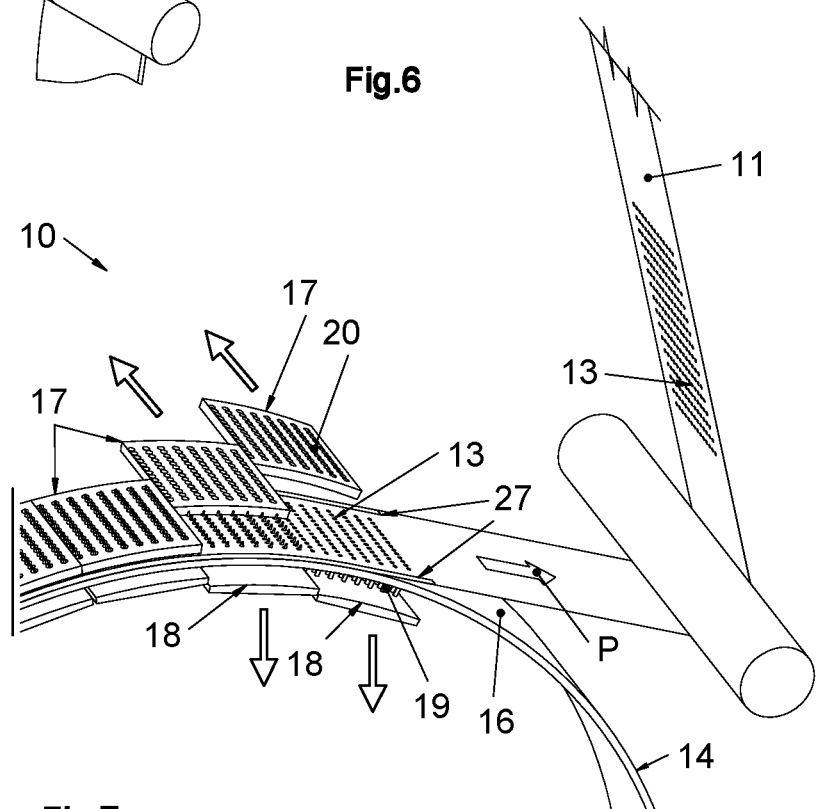
Figure 8:
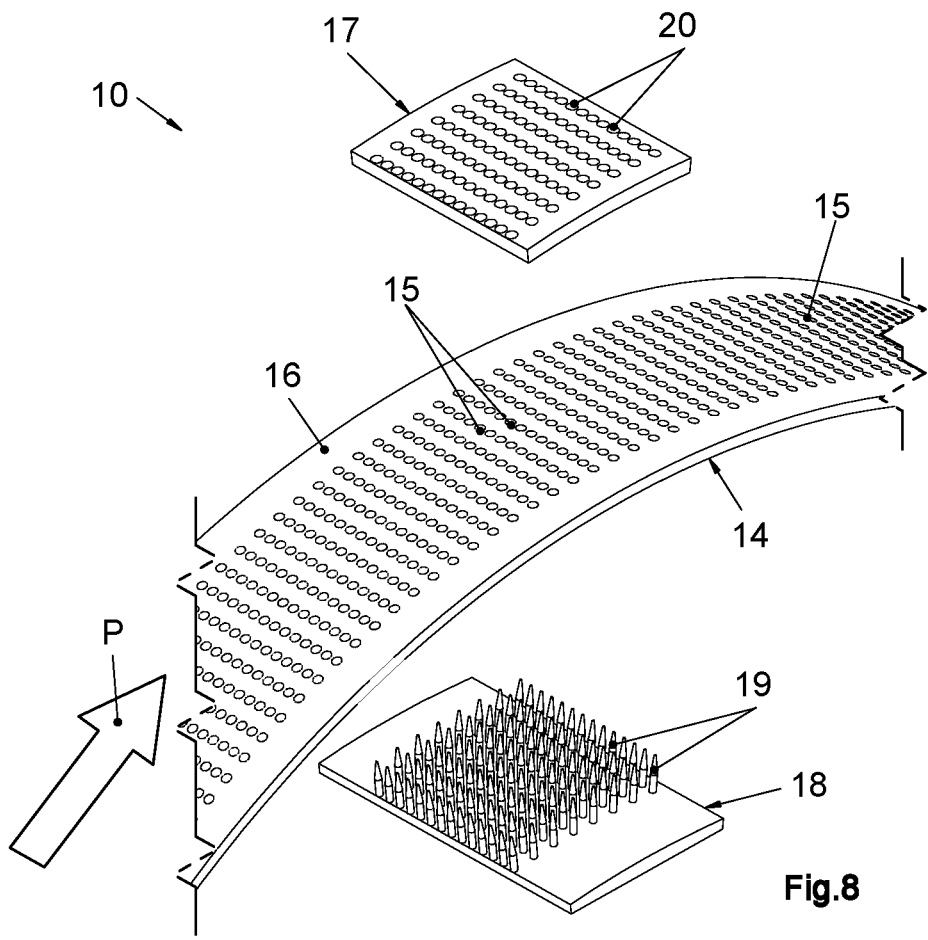
FIG. 8 schematically illustrates in exploded form a portion of a perforating apparatus according to a possible embodiment of the present invention.
Figure 9:
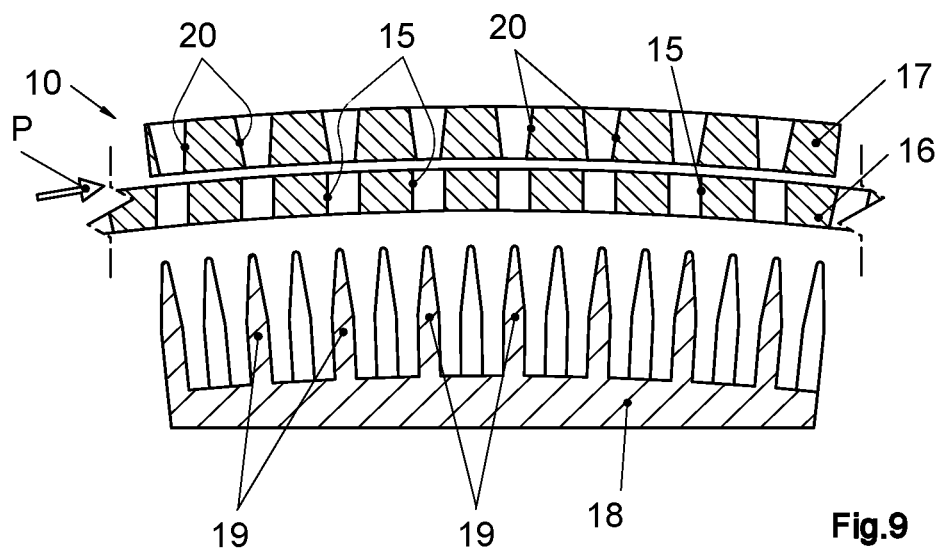
FIG. 9 schematically illustrates in cross-section a portion of a perforating apparatus according to a possible embodiment of the present invention.
Figure 10:
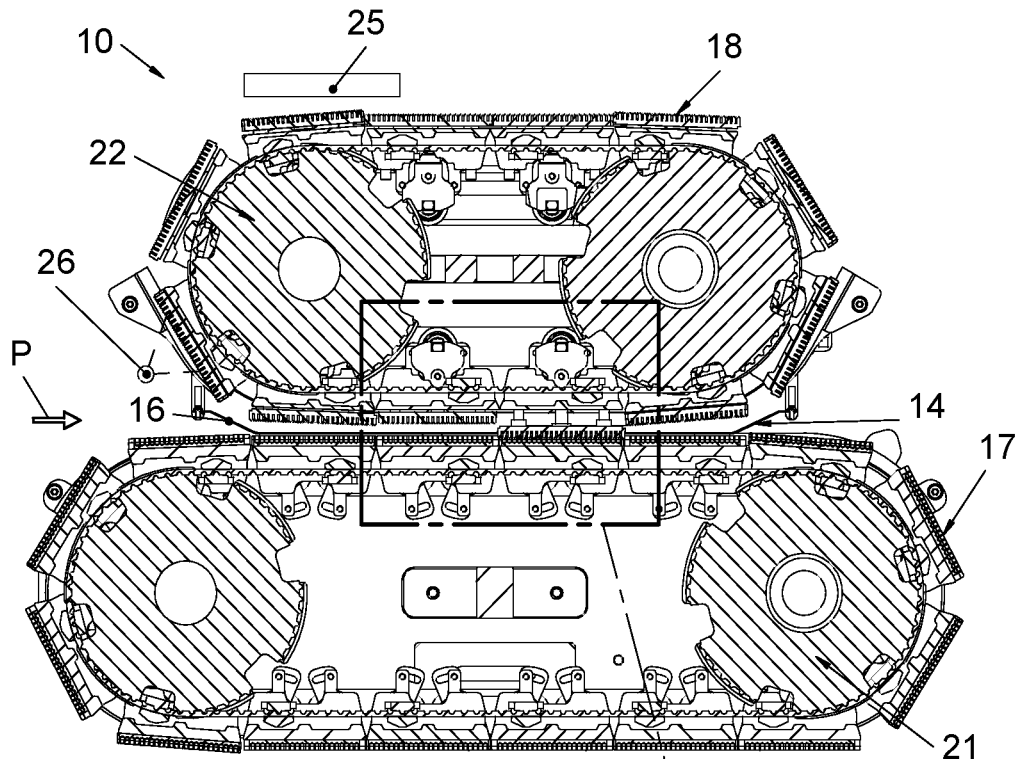
FIG. 10 schematically illustrates in cross-section a possible embodiment of a perforating apparatus according to the present invention.
Figure 11:
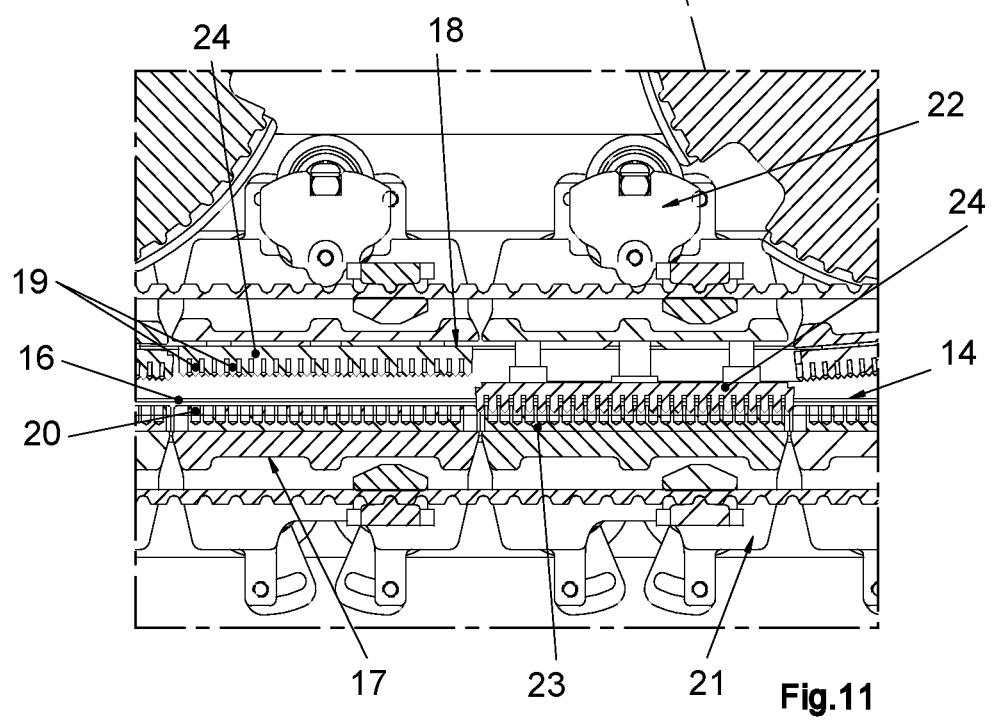
FIG. 11 schematically illustrates a detail of FIG. 10, wherein there is a pair of deformation members in the tracking position and a pair of deformation members in the coupling position.

With reference to FIG. 3, the web 11 has a plurality of holes 13 made according to a possible embodiment of the present invention, wherein there are none of the imperfections of the web 11 illustrated in FIG. 2 such as elongate profiles.

According to possible embodiments, the web 11 may comprise one or more layers and if necessary even elastic material. For example, the elastic material may comprise elastic threads, elastic films, elastic bands, or other.

According to possible embodiments, the perforating apparatus 10 comprises at least one first deformation member 17 provided with a plurality of openings 20.

In accordance with possible embodiments, the perforating apparatus 10 comprises at least one second deformation member 18 provided with protruding elements 19.

The openings 20 and the protruding elements 19 are joined together so as to cooperate, in use, to couple with the web 11 and make the plurality of holes 13.

The openings 20 may comprise through openings, or grooves having a depth such as to allow the respective protruding element 19 to enter the opening 20 without striking the bottom of the opening 20.

According to possible embodiments, the first deformation member 17 and the second deformation member 18 are configured to position themselves at least in a tracking position, wherein the first deformation member 17 and the second deformation member 18 are placed on opposite sides of the advancement path P and facing each other. For example, in the tracking position, in use, the first deformation member 17 and the second deformation member 18 are each facing towards a respective face of the web 11 while it advances along the advancement path P.

In accordance with possible embodiments, the first deformation member 17 and the second deformation member 18 are configured to position themselves in a coupling position, wherein the protruding elements 19 are coupled with the openings 20 orthogonally to the advancement path P to make, in use, a plurality of holes 13 in a zone of the web 11.

The movement of the first deformation member 17 and of the second deformation member 18 before and during the engagement with the web 11 combined with the coupling orthogonally to the advancement path P is advantageous and synergic for obtaining precise and circular holes 13, while the web 11 advances without the latter being locally slowed and deformed.

In the coupling position the protruding elements 19 are facing towards the first deformation member 17 and inserted in the relative openings 20.

In accordance with possible embodiments, the first deformation member 17 and/or the second deformation member 18 may have a suction system for sucking the web 11 so that in use the latter is retained in position.

According to possible embodiments, the suction system may comprise a plurality of suction holes arranged on the surface of the first deformation member 17 and/or on the surface of the second deformation member 18 facing towards the advancement path P, wherein the suction holes are fluidly connected to a suction source configured to suck, in use, the web 11 and retain it in position on the desired surface facing towards the advancement path P.

For example, the suction holes may be arranged on the surface of the first deformation member 17 in the spaces available between the openings 20, or inside the latter.

According to possible embodiments, the perforating apparatus 10 comprises a first movement unit 21 configured to move the first deformation member 17 at least along a portion parallel to the advancement path P.

In accordance with possible embodiments, the perforating apparatus 10 comprises a second movement unit 22 configured to move the second deformation member 18 at least along a portion parallel to the advancement path P.

According to possible embodiments, the first movement unit 21 and the second movement unit 22 are configured to be driven by means of two independent motor members.

For example, the first movement unit 21 and the second movement unit 22 may each comprise a track system provided with a pair of pulleys and a movable track coupled with the pulleys and on which the first deformation member 17 and the second deformation member 18 respectively are connected.

According to possible embodiments, the first movement unit 21 may be configured to move the first deformation member 17 orthogonally to the advancement path P, even while the first deformation member 17 is moved along a portion parallel to the advancement path P.

According to possible embodiments, the second movement unit 22 may be configured to move the second deformation member 18 orthogonally to the advancement path P, even while the second deformation member 18 is moved along a portion parallel to the advancement path P.

For example, the movement orthogonal to the advancement path P by the first deformation member 17 and/or by the second deformation member 18 may be obtained by means of a cam present in the track system which brings the first deformation member 17 and/or the second deformation member 18 into contact with the web 11 along a direction orthogonal to the advancement path P, while the first deformation member 17 and/or the second deformation member 18 travel along the portion parallel to the advancement path P.

According to possible embodiments, the movement orthogonal to the advancement path by the first deformation member 17 and/or by the second deformation member 18 may be obtained by means of a pusher, a piston, an articulated system, a combination thereof, or other.

In accordance with possible embodiments, the second movement unit 22 may be configured to move the second deformation member 18 orthogonally to the advancement path P, even while the first movement member 17 is moved along a portion parallel to the advancement path P, and the first movement unit 21 may be configured to move the first deformation member 17 exclusively along a defined path which comprises at least one portion parallel to the advancement path P.

In this case, the coupling position is reached by moving exclusively the second deformation member 18 orthogonally to the advancement path P.

If the advancement path P comprises a curved portion, the parallel portion along which the first deformation member 17 and the second deformation member 18 is moved is defined so that it follows the profile of the curved portion of the advancement path P.

For example, along the parallel portion the first deformation member 17 follows the profile of the curved portion with a first radius of curvature and the second deformation member 18 follows the profile of the curved portion with a second radius of curvature different from the first radius of curvature.

In this case, if the engagement position is reached in correspondence with the curved portion of the advancement path P the first deformation member 17 and the second deformation member 18 are shaped so that the respective openings 20 and the protruding elements 19 are oriented orthogonally to the advancement path P of the web 11.

According to possible embodiments, the first deformation member 17 and the second deformation member 18 may be moved by means of a common movement unit configured to move both of the deformation members 17 and 18 in a coordinated way.

The movement unit, whether it relates to each deformation member 17 and 18, or to both, is configured to move the deformation members 17 and 18 at least to couple them with the web 11 so as to make the plurality of holes 13 in the desired zone of the web 11.

For example, the first movement unit 21 and the second movement unit 22 may each comprise an actuator, a motor, a motion conversion device, combinations thereof, or other.

In accordance with one aspect of the present invention, the first deformation member 17 and the second deformation member 18, in the tracking position and in the coupling position, are configured to advance along a portion parallel to the advancement path P at the advancing velocity so as to make the plurality of holes 13 with relative velocities, at least along the advancement path P, between the first deformation member 17 and the web 11 and between the second deformation member 18 and the web 11 which are substantially zero.

In use, the first deformation member 17 and the second deformation member 18 in the tracking position and in the coupling position advance with relative velocities with respect to the web 11 that are substantially zero along the advancement path P.

In other words, at least for a portion of the advancement path P, the first deformation member 17 and the second deformation member 18 advance at the same advancing velocity as the web 11.

That allows the holes 13 to be made in the moving web 11 while keeping the first movement member 17 and the second movement member 18 in a movable reference system integral with the web 11 itself.

That makes it possible to not slow the web 11 and to keep the same velocity between the web 11 and the deformation members 17 and 18 along an advancement path P so as to avoid obtaining holes 13 having elongate shapes.

The possibility given by the present invention to advance the web 11 and make the holes 13 by engaging the web 11 orthogonally and keeping the substantially zero relative velocities at least along the advancement path P between the first deformation member 17 and the web 11 and between the second deformation member 18 and the web 11, allows the obtainment of holes 13 having a substantially circular and not elliptical shape.

According to possible embodiments, the first deformation member 17 comprises a first plate 23 wherein the openings 20 are present and the second deformation member 18 comprises a second plate 24 wherein the protruding elements 19 are present.

In accordance with possible embodiments, the plates 23 and 24 may be connected to the relative movement unit 21 and 22 by means of suitable connecting elements.

For example, in the case of a track system, the connecting elements may be connected to the relative deformation member 17 and 18 and in turn to the track of the track system.

According to possible embodiments, the perforating apparatus 10 comprises disengaging means 14 interposed between the first deformation member 17 and the second deformation member 18 in the coupling position configured to disengage the web 11 from the protruding elements 19 so that the perforated web 11 is freed from the protruding elements 19.

That aspect is advantageous because it allows the perforated web 11 to be rapidly and easily freed from the protruding elements 19. Actually, the perforated web 11 may be retained in position for example, by disengaging means 14 which act as an opposing element, or pushed towards the opposite direction from which the protruding elements 19 come out of the perforated web 11 to disengage from the latter.

In accordance with possible embodiments, the disengaging means 14 may be fixed.

According to possible embodiments, the disengaging means 14 may be configured to adopt an operating position, wherein the disengaging means 14 are interposed between the first deformation member 17 and the second deformation member 18 in the coupling position.

In accordance with possible embodiments, the disengaging means 14 may be configured to adopt a home position, wherein the disengaging means 14 are not interposed between the first deformation member 17 and the second deformation member 18 in the coupling position.

According to possible embodiments, the disengaging means 14 may be movable at least between the operating position and the home position.

In accordance with possible embodiments, the disengaging means 14 may comprise a disengaging element 16 provided with at least one through opening 15 wherein in the coupling position the protruding elements 19 are inserted.

According to possible embodiments, the disengaging element 16 may comprise a plate which acts as a mechanical opposing element to the perforated web 11 and allows the protruding elements 19 to easily disengage the web 11.

In accordance with possible embodiments, the disengaging means 14 may comprise nozzles configured to emit a fluid in the direction opposite to the direction of disengagement of the protruding elements 19.

The direction of disengagement of the protruding elements 19 is the direction opposite to that of engagement with the web 11 for positioning in the coupling position.

According to possible embodiments, the disengaging element 16 may comprise a plurality of through openings 15 arranged in one or more zones of the disengaging element 16 itself.

According to possible embodiments, the disengaging element 16 may be configured to advance the web 11 by moving in the direction defined by the advancement path P and bringing with it the web 11 itself, or may act as a support during advancing of the web 11 along the advancement path P which occurs by means of advancing means.

The advancing means may comprise driven rollers and/or idle rollers, or other elements suitable for advancing the web 11 along the advancement path P.

For example, the disengaging element 16 may comprise a drum defining along at least part of its perimeter a curved portion of the advancement path P.

According to possible embodiments, the drum may be configured to rotate around an axis of rotation by means of suitable actuating means.

For example, the drum may be connected to an actuator, to a motor, to a motion conversion device, or other.

In accordance with possible embodiments, the first deformation member 17 and the second deformation member 18 are configured to couple with the web 11 jointly in correspondence with the through opening 15 to make a plurality of holes 13 in a zone of the web 11.

According to possible embodiments, the perforating apparatus 10 comprises a heating device 25 configured to heat the protruding elements 19.

In accordance with possible embodiments, the heating device may comprise a heating element having a heating surface oriented at least in one portion towards the protruding elements 19 and configured to heat the latter.

For example, the heating element may be a radiant heat lamp, a hot air emitter, an electromagnetic induction heating device, combinations thereof, or other similar or comparable heating elements.

According to possible embodiments, the protruding elements 19 and/or the openings 20 may be heated to make a plurality of holes 13.

For example, the protruding elements 19 and/or the openings 20 may be heated by means of a heating device 25 integrated in the first deformation member 17 and/or in the second deformation member 18.

According to possible embodiments, the heating device 25 may be configured to bring the temperature of the protruding elements 19 and/or of the openings 20 to a desired temperature.

For example, the temperature may be greater than the melting threshold of at least one of the components which constitute the web 11.

According to possible embodiments, a heating device 25 may be placed in correspondence with the infeed zone wherein the web 11 advances, in use, along the advancement path P between at least one first deformation member 17 and one second deformation member 18.

That heating device 25 is configured to heat the web 11 so as to facilitate the making of the holes 13 by means of the first deformation member 17 and the second deformation member 18.

According to possible embodiments, the perforating apparatus 10 may comprise a measuring device 26 configured to measure the temperature of the protruding elements 19.

According to possible embodiments, the perforating apparatus 10 may comprise a measuring device 26 configured to measure the temperature of the web 11.

For example, the measuring device 26 may comprise a thermal camera, a pyrometer, or a temperature sensor of another type.

In accordance with possible embodiments, the perforating apparatus 10 may comprise retaining means 27 placed along two directions parallel to the advancement path P, arranged laterally to the zone of the web 11 wherein, in use, the holes 13 are made.

According to possible embodiments, the retaining means 27 are configured to position themselves in contact with the web 11 for retaining the web 11 in contact with the first deformation member 17 or the second deformation member 18, or in contact with the disengaging means 14.

That aspect allows the web 11 to be kept spread out so that the ends do not move, or do not retract towards the centre of the web 11, for example in the case of an elastic web 11.

In accordance with possible embodiments, the perforating apparatus 10 may comprise a plurality of first deformation members 17 and a plurality of said second deformation members 18, wherein each of the first deformation members 17 and of the second deformation members 18 is configured to move independently of the others.

That aspect allows the achievement of high levels of production flexibility which allow various and different pluralities of holes 13 to be made in one or more predetermined zones of the web 11 as it advances.

Depending on the type of plurality of holes 13 to be made and the zone of the web 11 wherein the latter is to be made, it is possible to operate one or more deformation members 17 and 18 in a coordinated way, so as to obtain a web 11 having the desired pluralities of holes 13 in the desired zones of the web 11.

For example, it is possible to make a plurality of intermittent holes 13 in the web 11 so as to alternate zones provided with holes 13 and zones without holes 13.

According to possible embodiments, at least part of the surface of the first deformation member 17 oriented, in the tracking position, towards the second deformation member 18 is coated with a coating comprising silicone material.

In accordance with possible embodiments, the first deformation member 17 and/or the second deformation member 18 are configured to position themselves along a direction transverse to the advancement path P so that the first deformation member 17 and the second deformation member 18 are partially overlapping each other.

In accordance with possible embodiments, the first deformation member 17 and/or the second deformation member 18 are configured to position themselves along a direction transverse to the advancement path P so that the first deformation member 17 and the second deformation member 18 are at least partially overlapping each other.

According to possible embodiments, the first deformation member 17 may be configured to move along a direction transverse to the advancement path P at least between a first wait position, wherein the first deformation member 17 is placed at the side of the zone wherein the web 11 advances in use, and a second operating position, wherein the first deformation member 17 is at least partially overlapping the zone wherein the web 11 advances in use.

The movement between the first wait position and the second operating position of the first deformation member 17 may be obtained by means of the first movement unit 21.

That aspect allows compact dimensions and allows the first deformation member 17 to be positioned in the desired position in relation to the zone of the web 11 wherein the holes 13 are to be made.

The first deformation member 17 positioning itself in the first wait position allows the use of space typically not used and wherein there are no other components which can interfere with the first deformation member 17.

According to possible embodiments, the second deformation member 18 may be configured to position itself at least in a wait position, wherein it does not interfere with the web 11 in transit, and at least an operating position, wherein it is coupled with the web 11.

According to possible embodiments, the present invention also relates to a process for perforating at least one web 11, comprising:

- advancing the web 11 along an advancement path P at an advancing velocity;
- positioning at least one first deformation member 17 provided with a plurality of openings 20 and at least one second deformation member 18 provided with a plurality of protruding elements 19 in a tracking position, wherein the first deformation member 17 and the second deformation member 18 are placed on opposite sides of the advancement path P and facing each other facing towards two opposite surfaces of the web 11;
- advancing the first deformation member 17 and the second deformation member 18 along a portion parallel to the advancement path P at the advancing velocity, so that the relative velocities, at least along the advancement path P, between the first deformation member 17 and the web 11 and between the second deformation member 18 and the web 11 are substantially zero;
- positioning the first deformation member 17 and the second deformation member 18 in a coupling position, wherein the protruding elements 19 are coupled with the openings 20 orthogonally to the advancement path P with the web 11 interposed between them to make a plurality of holes 13 in a zone of the web 11, while the first deformation member 17 and the second deformation member 18 advance at the advancing velocity along a portion parallel to the advancement path P so that the relative velocities remain substantially zero.

That aspect allows the obtainment of holes 13 in a web 11 rapidly and as the web 11 advances along an advancement path P directly in line.

In accordance with possible embodiments, the process provides that the first deformation member 17 and/or the second deformation member 18 are positioned along a direction transverse to the advancement path P so that the first deformation member 17 and the second deformation member 18 are partially overlapping each other to couple with the web 11 and make the plurality of holes 13 in a zone of the web 11, wherein the zone extends along the transverse direction for an extension less than the transverse extension of the web 11 relative to the advancement path P.

In accordance with possible embodiments, the process provides that the first deformation member 17 and/or the second deformation member 18 are positioned along a direction transverse to the advancement path P so that the first deformation member 17 and the second deformation member 18 are at least partially overlapping each other to couple with the web 11 and make the plurality of holes 13 in a zone of the web 11, wherein the zone extends along the transverse direction for an extension less than the transverse extension of the web 11 relative to the advancement path P.

According to possible embodiments, the process provides that the protruding elements 19 are heated by means of a heating device 25.

According to possible embodiments, the process provides that disengaging means 14 disengage the web 11 from the protruding elements 19 so as to free the web 11 from the protruding elements 19.

According to possible embodiments, the process provides that retaining means 27 position themselves in contact with the web 11 along two directions parallel to the advancement path P, arranged laterally to the zone of the web 11 wherein holes 13 are made to retain the web 11 in contact with the first deformation member 17 or the second deformation member 18, or in contact with the disengaging means 14.

According to possible embodiments, the retaining means 27 may comprise a pair of elements positionable in contact with the web, such as belts, bars, rollers, plates, or other elements configured to transversally retain the web 11 and to allow it to advance along the advancement path P.

According to possible embodiments, the present invention also relates to a machine for producing sanitary absorbent articles comprising at least one perforating apparatus 10 according to any of the possible embodiments.

That aspect allows a plurality of holes 13 to be made in a web 11 as it advances directly in line and simultaneously guarantees reduced likelihoods of the web 11 being able to accidentally become caught in the apparatus 10 itself or in another component of the production machine.

That aspect also makes it possible to avoid using already perforated webs which involve large warehouse spaces and costs, high disposal costs due to their deterioration and poor flexibility in making different types of holes 13.

It is clear that the perforating apparatus 10, the perforating process and the machine for producing sanitary absorbent articles comprising at least one perforating apparatus 10 described above may be subject to modifications and/or additions of parts, without thereby departing from the scope of the present invention.

It is also clear that the first deformation member 17 and the second deformation member 18 have been described, for expository purposes only and without limiting the scope of the invention, in relation to the possible embodiment illustrated in the drawings.

It is also clear that the characteristics regarding the first deformation member 17 and the second deformation member 18 may be applied to inverted parts without thereby departing from the scope of the present invention.

The considerations and the embodiments described herein for the first deformation member 17 may be valid for the second deformation member 18, and vice versa without thereby departing from the scope of the present invention.

It is also clear that, although the present invention has been described with reference to some specific examples, a person skilled in the art will certainly be able to make many other equivalent embodiments of the perforating apparatus 10, of the perforating process and of the machine for producing sanitary absorbent articles comprising at least one perforating apparatus 10 having the characteristics expressed in the claims and therefore all covered by the scope of protection that they define.

In the claims below, references in brackets are intended only to facilitate reading and must not be considered to be limiting factors as regards the scope of protection of the specific claims.

The invention claimed is:

1. A perforating apparatus for perforating at least one web advancing along an advancement path at an advancing velocity, comprising:
   at least one first deformation member provided with a plurality of openings and at least one second deformation member provided with a plurality of protruding elements,
   wherein said first deformation member and said second deformation member are configured to position themselves at least in a tracking position,
   wherein said first deformation member and said second deformation member are placed on opposite sides of said advancement path and facing each other, and to position themselves in a coupling position downstream of the tracking position relative to the advancement path,
   wherein said protruding elements are coupled with said openings orthogonally to said advancement path to make, in use, a plurality of holes in a zone of said web, and
   wherein said first deformation member and said second deformation member, in said tracking position and in said coupling position, are configured to advance along a portion parallel to said advancement path at said advancing velocity, such that the first and second deformation members move in a same direction and at a substantially same speed as the at least one web in both the tracking position and coupling position so as to make said plurality of holes with substantially zero relative velocities, at least along said advancement path, between said first deformation member and said web and between said second deformation member and said web.

2. The apparatus of claim 1, wherein said first deformation member comprises a first plate, and wherein said openings are present and said second deformation member comprises a second plate wherein said protruding elements are present.

3. The apparatus of claim 1, further comprising disengaging means interposed between said first deformation member and said second deformation member in said coupling position and configured to disengage said web from said protruding elements so that, in use, said perforated web is freed from said protruding elements.

4. The apparatus of claim 3, wherein said disengaging means comprise at least one disengaging element provided with at least one through opening, and wherein in said coupling position said protruding elements are inserted.

5. The apparatus of claim 1, further comprising a heating device configured to heat said protruding elements.

6. The apparatus of claim 3, further comprising retaining means placed along two directions parallel to said advancement path arranged laterally to said zone of said web; and
wherein, in use, said holes are made, wherein, in use, said retaining means are configured to position themselves in contact with said web for retaining said web in contact with said first deformation member, or said second deformation member, or in contact with said disengaging means.

7. The apparatus of claim 1, further comprising a plurality of said first deformation members and a plurality of said second deformation members, wherein each of said plurality of first deformation members and of said plurality of second deformation members is configured to move independently of the others.

8. The apparatus of claim 1, wherein at least part of a surface of said first deformation member oriented, in said tracking position, towards said second deformation member, is coated with a coating comprising silicone material.

9. The apparatus of claim 1, wherein said first deformation member and/or said second deformation member are configured to position themselves along a direction transverse to said advancement path so that said first deformation member and said second deformation member are at least partially overlapping each other.

10. A process for perforating at least one web, comprising:
advancing said web along an advancement path at an advancing velocity;
positioning at least one first deformation member provided with a plurality of openings and at least one second deformation member provided with a plurality of protruding elements in a tracking position, wherein said first deformation member and said second deformation member are placed on opposite sides of said advancement path and facing each other facing towards two opposite surfaces of said web;
advancing said first deformation member and said second deformation member along a portion parallel to said advancement path at said advancing velocity to a coupling position, so that relative velocities, at least along said advancement path, between said first deformation member and said web and between said second deformation member and said web are substantially zero;
positioning said first deformation member and said second deformation member in the coupling position, wherein said plurality of protruding elements are coupled with said plurality of openings orthogonally to said advancement path with said web interposed between them to make a plurality of holes in a zone of said web, while said first deformation member and said second deformation member advance at said advancing velocity along a portion parallel to said advancement path so that said relative velocities remain substantially zero,
wherein the first and second deformation members move in a same direction and at a substantially same speed as the at least one web in both the tracking position and coupling position.

11. The process of claim 10, wherein said first deformation member and/or said second deformation member are positioned along a direction transverse to said advancement path so that said first deformation member and said second deformation member are at least partially overlapping each other to couple with said web and make said plurality of holes in the zone of said web, and
wherein said zone extends along said transverse direction for an extension less than a transverse extension of said web relative to said advancement path.

12. The process of claim 10, wherein said protruding elements are heated by a heating device.

13. The process of claim 10, further comprising using disengaging means to disengage said web from said protruding elements so as to free said web from said protruding elements.

14. The process of claim 10, wherein retaining means position themselves in contact with said web along two directions parallel to said advancement path arranged laterally to said zone of said web, and wherein said holes are made to retain said web in contact with said first deformation member or said second deformation member.

15. A machine for producing sanitary absorbent articles comprising at least one perforating apparatus according to claim 1.

* * * * *